US00PP26115P3

(12) United States Plant Patent
Egger

(10) Patent No.: US PP26,115 P3
(45) Date of Patent: Nov. 17, 2015

(54) ***SEDUM* PLANT NAMED 'TOUCHDOWN JADE'**

(50) Latin Name: *Sedum telephium (Syn. Hylotelephium telephium)*
Varietal Denomination: Touchdown Jade

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 229 days.

(21) Appl. No.: 13/998,103

(22) Filed: Sep. 30, 2013

(65) Prior Publication Data

US 2015/0096092 P1 Apr. 2, 2015

(51) Int. Cl.
*A01H 5/02* (2006.01)

(52) U.S. Cl.
USPC ..... Plt./479
CPC ..... *A01H 5/02* (2013.01)

(58) Field of Classification Search
USPC ..... Plt./479
See application file for complete search history.

(56) References Cited

PUBLICATIONS

Germania Seed Company. Emerald Coast—Ornamental Grasses and Perennials, retrieved on Jun. 18, 2015, retrieved from the Internet at <https://www.germaniaseed.com/pdf/2014/722_emeraldcoast.pdf> (2013-2014) pp. 1-13.*

Greenhouse Grower. Terra Nova Nurseries Announces New *Sedum* Touchdown Collection Aug. 15, 2013 retrieved on Jun. 17, 2015, retrieved from the Internet at <http://www.greenhousegrower.com/varieties/terra-nova-nurseries-announces-new-sedum-touchdown-collection/> 5 pp.*

* cited by examiner

*Primary Examiner* — June Hwu
(74) *Attorney, Agent, or Firm* — Klarquist Sparkman, LLP

(57) ABSTRACT

A new and distinct hybrid of *Sedum* plant substantially as shown and described, with light pink flowers in large inflorescences, blue green leaves with rose red main veins, strong rose pink stems, orange carpels when the seed is developing, a multiple crown, dense, low, mounding habit, and excellent vigor.

2 Drawing Sheets

Botanical denomination: *Sedum telephium* (Syn. *Hylotelephium telephium*).

Variety designation: 'Touchdown Jade'.

BACKGROUND OF THE INVENTION

The present invention relates to a new and distinct cultivar of *Sedum telephium* and given the cultivar name of 'Touchdown Jade'. *Sedum* is in the family Crassulaceae. The new cultivar is part of a planned breeding program to make short, compact, multicrown plants. The new cultivar originated from an open pollinated cross of a proprietary seedling, *Sedum* 384-2.

Compared to the seed parent, *Sedum* 384-2, the new cultivar, has a better habit and larger inflorescences.

Compared to *Sedum* 'Desert Blonde', U.S. Plant Pat. No. 24,901, the new cultivar has light pink flowers rather than creamy white.

Compared to *Sedum* 'Yellow Xenox', U.S. Plant Pat. No. 21,528, the new variety is has light pink flowers rather than cream, a wider habit, with more crowns from young plants (an advantage to a nursery grower as the plants fill the pots quickly).

This new and unique *Sedum* is distinguished by:

1. light pink flowers in large inflorescences,
2. blue green leaves with rose red main veins,
3. strong rose pink stems,
4. orange carpels when the seed is developing, 5. a multiple crown, dense, low, mounding habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows an 18 month old plant of *Sedum* 'Touchdown Jade' in the garden in late May in Canby, Oreg.

FIG. 2 shows a 10 month old plant in flower and fruit in the trial field in late August in Canby, Oreg.

DETAILED PLANT DESCRIPTION

Figure 3:
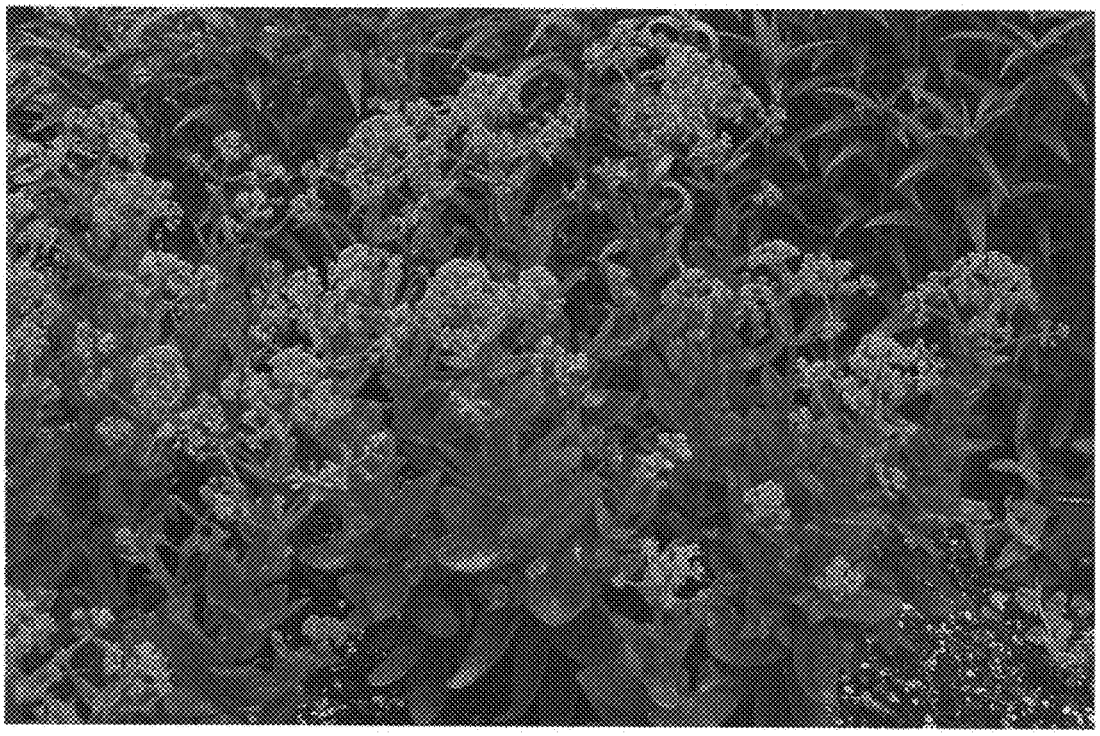
FIG. 3 shows a 3 year old plant of the new variety in July grown in hotter and sunnier conditions showing the red tints on the leaves and veins, and the rose pink stems.

The following is a detailed description of the new *Sedum* hybrid based on observations of 10 month old specimens grown in the trial bed in full sun under typical outdoor conditions in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart,* 5$^{th}$ edition.

Plant:

*Type.*—Herbaceous perennial.

*Hardiness.*—USDA Zone 4 to 9.

*Size.*—22 cm tall from the ground to the base of the inflorescence and 48 cm wide.

*Habit.*—Low, clumping mound.

*Vigor.*—Excellent.

Stem:

*Number.*—About 8.

*Size.*—13 cm long and 6 mm wide.

*Internode length.*—4 cm to 5 cm long.

*Color.*—Closest to Yellow Green 147C in shade and Greyed Purple 184B in sun.

*Texture.*—Succulent.

*Surface.*—Glabrous.

Leaf:

*Type.*—Simple.

*Arrangement.*—Opposite.

*Shape.*—Ovate.

*Apex.*—Obtuse.

*Base.*—Obtuse.

*Venation.*—Pinnate.

*Margins.*—Entire to slightly serrate, tinted Red Purple 187B.

*Blade size.*—Grows to 11 cm long and 5.8 cm wide.

*Surface.*—Glabrous on both sides.

*Texture.*—Thick, spongy, succulent.

*Petiole.*—Leaves sessile.

*Leaf color.*—Topside Green 137B with the vein 147D in low light and tinted Greyed Purple 187A when grown in high light with the vein 187B; bottom side Green 138B with vein 147D (tinted Greyed Purple 187B in very high light).

Inflorescence:

*Type.*—Terminal, corymbose, umbel-like.

*Number of flowers.*—About 500.

*Peduncle.*—13 cm long and 6 mm wide, with internodes 4 cm to 5 cm long, succulent, glabrous, closest to Yellow Green 147C in shade and Greyed Purple 184B in sun.

*Pedicels.*—2 mm to 3 mm long, 1 mm wide, glabrous, Yellow Green 148B.

*Rachis.*—Grows to 8 cm tall and 6 mm wide, Greyed Purple 184B in sun, Yellow Green 147D where shaded, glabrous.

*Size.*—Grows to 10 cm deep and 12 cm wide.

*Bloom period.*—August through September in Canby, Oreg.

Flower bud:

*Size.*—2.5 mm wide, 4 mm deep.

*Description.*—Ovoid.

*Color.*—Greyed Red 182C.

Flower:

*Type.*—Actinomorphic.

*Shape.*—Stellate.

*Size.*—5 mm deep and 5 mm wide.

*Corolla description.*—5 mm deep and 5 mm wide, 5 petals, each lanceolate, 4.5 mm long and 1.5 mm wide, margins entire, tip acuminate, glabrous on both sides, topside Red Purple 65C and bottom side Red Purple 65C on top half blending to White N155C.

*Calyx description.*—1.5 mm deep and 3 mm wide, stellate, 5 lobes, divided to the base, margins entire, tip acute, glabrous, Yellow Green 148B on both sides.

*Stamen description.*—10, 2.5 mm long, filaments 2.4 mm long and White NN155C, anthers sterile and reduced Grey Brown N199A, no pollen.

*Pistil description.*—5 separate prominent carpels, each 4 mm deep and 1.5 mm wide, ovary 2 mm long, White NN155C except top where Red Purple 61A, style 2 mm long, stigma and style Red Purple 61A.

*Fragrance.*—None.

*Lastingness.*—Each stem lasts up to a month.

Fruit:

*Type.*—Ventrally dehiscent follicle, erect, attenuate.

*Fertility.*—Low.

*Size.*—3 mm wide and 4 mm deep.

*Color.*—Greyed Orange N170A.

Seed: None seen.

Disease and pest resistance or tolerance: Pest and disease resistance are typical for this type of *Sedum*. No known resistances.

I claim:

1. A new and distinct hybrid of *Sedum* plant as herein illustrated and described.

* * * * *

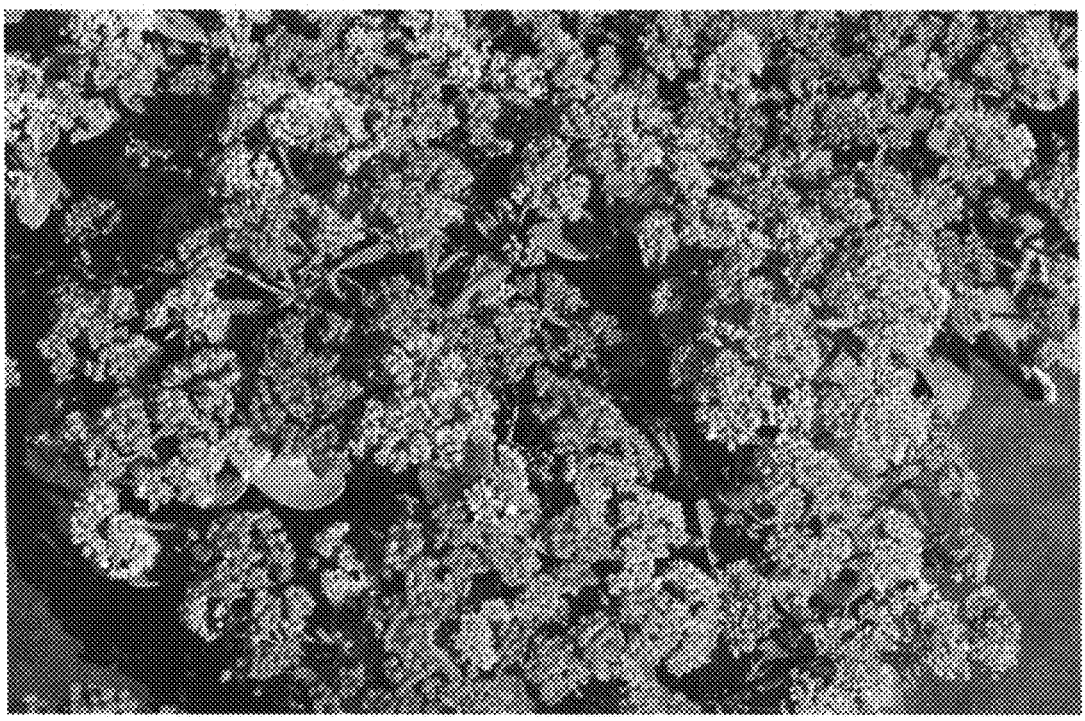

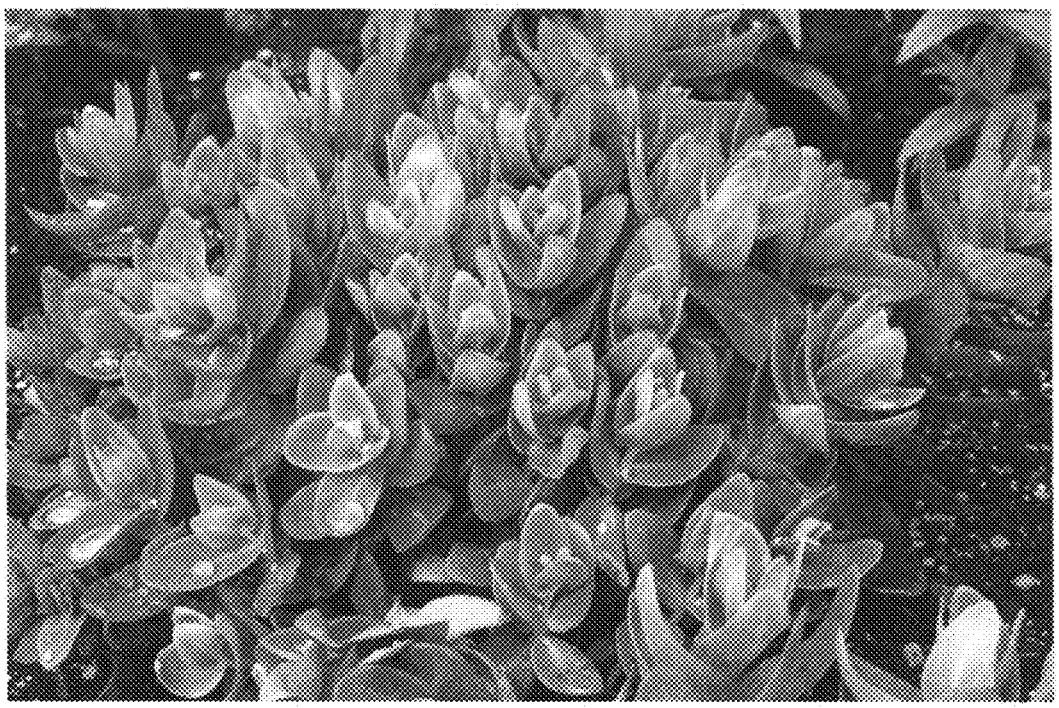
FIG. 1 above, FIG. 2 below